United States Patent
Lopez de Leon et al.

(10) Patent No.: US 9,771,569 B2
(45) Date of Patent: Sep. 26, 2017

(54) POLYPEPTIDES HAVING XYLANASE ACTIVITY AND POLYNUCLEOTIDES ENCODING SAME

(71) Applicant: Novozymes A/S, Bagsvaerd (DK)

(72) Inventors: Alfredo Lopez de Leon, Davis, CA (US); Michael Rey, Davis, CA (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/146,162

(22) Filed: May 4, 2016

(65) Prior Publication Data

US 2016/0237417 A1  Aug. 18, 2016

Related U.S. Application Data

(62) Division of application No. 14/605,764, filed on Jan. 26, 2015, now Pat. No. 9,353,360, which is a division of application No. 12/941,474, filed on Nov. 8, 2010, now Pat. No. 8,940,515, which is a division of application No. 12/327,439, filed on Dec. 3, 2008, now Pat. No. 7,851,193.

(60) Provisional application No. 60/992,565, filed on Dec. 5, 2007.

(51) Int. Cl.
| | |
|---|---|
| *C12N 9/42* | (2006.01) |
| *C12N 9/30* | (2006.01) |
| *C12N 9/24* | (2006.01) |
| *C12P 21/06* | (2006.01) |
| *C12P 19/34* | (2006.01) |
| *C07H 21/04* | (2006.01) |
| *C07K 1/00* | (2006.01) |
| *C12N 15/82* | (2006.01) |
| *C12P 19/14* | (2006.01) |
| *C12P 19/02* | (2006.01) |

(52) U.S. Cl.
CPC ......... *C12N 9/2482* (2013.01); *C12N 9/2402* (2013.01); *C12N 9/248* (2013.01); *C12N 15/8245* (2013.01); *C12N 15/8246* (2013.01); *C12P 19/02* (2013.01); *C12P 19/14* (2013.01); *C12Y 302/01008* (2013.01); *Y02P 20/52* (2015.11)

(58) Field of Classification Search
CPC  C12N 15/8245; C12N 15/8246; C12N 9/248; C12N 9/2402; C12N 9/2482; C12P 19/14; C12P 19/02; C12Y 302/01008; Y02P 20/52

USPC ..... 435/209, 203, 200, 69.1, 91.1; 536/23.1, 536/23.2; 530/350
See application file for complete search history.

(56) References Cited

U.S. PATENT DOCUMENTS

| | | | |
|---|---|---|---|
| 2006/0003433 | A1 | 1/2006 | Steer et al. |
| 2009/0042266 | A1 | 2/2009 | Vehmaanpera et al. |
| 2009/0148901 | A1 | 6/2009 | Lopez de Leon et al. |

FOREIGN PATENT DOCUMENTS

| | | |
|---|---|---|
| WO | 97027293 | 6/1997 |
| WO | 9727292 A1 | 7/1997 |
| WO | 0142433 A2 | 6/2001 |
| WO | 2006078256 | 7/2006 |
| WO | 2007071818 | 6/2007 |
| WO | 2009018537 | 2/2009 |

OTHER PUBLICATIONS

Broun et al., Science, vol. 282, pp. 1315-1317 (1998).
Sandal et al., Geneseq Accession No. AAW23541 (1998).
Merchant et al., Production of Xylanase by the Thermophilic Fungus *Thielavia terrestris*, 1988, Biotechnology Letters 10: 513-516.
Gilbert et al., A comparison of two xylanases from the thermophilic fungi *Thielavia terrestris* and *Thermoascus crustaceus*, 1993, Applied Microbiology and Biotechnology 40: 508-514.
Kvesitadze et al., Isolation and properties of a thermostable endoglucanase from a thermophilic mutant strain of Thielavia terrestris, 1995, Applied Biochemistry and Biotechnology, Humana Press, v. 50, No. 2: 137-143.
Polizeli et al., Xylanases from fungi: properties and industrial applications, 2005, Applied Microbiology and Biotechnology v. 67, No. 5: 577-591.
Berlin et al, 2007, Biotechnol Bioengg 97(2), 287-296.
Jeong et al, 2004, Canadian J. Microbial 50(10),835-843.
Iikura et al, 1997, Biosci Biotechnol Biochem 61(9), 1593-1595.
Seffernick et al, 2001, J Bacteriol 183(8), 2405-2410.
Whisstock et al, 2003, Qtr Rev Biophys 36(3), 307-340.
Witkowski et al, 1999, Biochemistry 38, 11643-11650.

*Primary Examiner* — Ganapathirama Raghu
(74) *Attorney, Agent, or Firm* — Robert Starnes

(57) ABSTRACT

The present invention relates to isolated polypeptides having xylanase activity and isolated polynucleotides encoding the polypeptides. The invention also relates to nucleic acid constructs, vectors, and host cells comprising the polynucleotides as well as methods of producing and using the polypeptides.

16 Claims, 4 Drawing Sheets

```
        M   H   L   A   S   A   L   L   F   L   A   S   L   P   L   G   L   A   G   K
1       ATGCATCTCGCCTCCGCGTTGCTCTTCCTCGCCTCGCTGCCCCTCGGGCTGGCGGGCAAG
        D   K   G   K   P   C   K   K   G   L   N   T   L   A   K   Q   A   G   L   K
61      GACAAGGGCAAGCCGTGCAAGAAGGGCCTCAACACGCTCGCCAAGCAGGCCGGCCTCAAG
        Y   F   G   S   A   T   D   S   P   G   F   R   E   R   A   G   Y   E   A   V
121     TACTTCGGCTCGGCCACCGACTCGCCGGGCTTCCGCGAGCGCGCCGGCTACGAGGCCGTG
        Y   P   Q   Y   D   Q   I   M   W   K   S   G   E   F   H   M   T   T   P   T
181     TACCCGCAGTACGACCAGATCATGTGGAAGTCGGGCGAGTTCCACATGACGACGCCCACC
        N   G   M   K   W   V   F   T   E   P   E   R   G   V   F   N   F   T   E   G
241     AACGGCATGAAGTGGGTCTTCACCGAGCCGGAGCGCGGCGTGTTCAACTTCACCGAGGGC
        E   I   V   A   S   L   A   K   Q   N   G   F   M   L   R   C   H   A   L   V
301     GAGATCGTGGCGTCGCTCGCCAAGCAGAACGGCTTCATGCTGCGCTGCCACGCGCTCGTC
        W   H   S   Q   L   P   D   W   V   T   A   T   N   W   T   A   A   E   L   R
361     TGGCACAGCCAGCTCCCCGACTGGGTCACGGCGACCAACTGGACCGCCGCTGAACTGCGC
        Q   I   I   V   N   H   I   T   H   V   V   G   H   W   K   G   Q   C   Y   A
421     CAGATCATCGTCAACCACATCACCCACGTGGTCGGCCATTGGAAGGGCCAGTGCTATGCC
        W   D   V   V   N   E   A   L   N   E   D   G   T   Y   R   D   S   I   F   Y
481     TGGGACGTCGTTAACGAGGCGCTCAACGAGGACGGCACCTACCGCGACTCCATCTTCTAC
        Q   V   L   G   E   E   Y   I   K   L   A   F   E   T   A   S   K   I   D   P
541     CAGGTGCTCGGCGAGGAGTACATCAAGCTGGCCTTTGAGACTGCCTCCAAGATTGACCCG
        H   A   K   L   Y   Y   N   D   Y   N   L   E   Y   P   G   P   K   V   T   G
601     CATGCCAAGCTGTACTACAACGACTACAACCTCGAGTATCCCGGCCCCAAGGTCACCGGC
        A   Q   N   I   V   K   M   L   K   T   A   G   I   R   I   D   G   V   G   L
661     GCCCAGAACATCGTCAAGATGCTCAAGACCGCTGGCATCCGCATCGACGGCGTCGGCCTG
        Q   S   H   L   V   A   E   S   H   P   T   L   D   Q   H   I   D   A   I   R
721     CAGTCGCACCTCGTCGCCGAGAGCCACCCGACGCTCGACCAGCACATCGACGCCATCCGG
        S   F   S   S   L   G   V   E   V   A   L   T   E   L   D   V   R   L   T   L
781     TCCTTCTCCAGCCTCGGCGTCGAGGTCGCCCTGACCGAGCTCGACGTCCGCCTGACGCTG
        P   A   N   A   T   N   L   A   E   Q   N   D   A   Y   K   N   I   V   G   A
841     CCCGCCAACGCGACGAACCTGGCCGAGCAGAACGACGCCTACAAGAACATCGTCGGCGCC
        C   V   Q   V   R   G   C   I   G   V   T   I   W   D   F   Y   D   P   F   S
901     TGCGTCCAGGTCCGCGGCTGCATCGGCGTCACCATCTGGGACTTCTACGACCCCTTCAGC
        W   V   P   A   T   F   P   G   Q   G   A   P   L   L   W   F   E   N   F   T
961     TGGGTCCCCGCCACCTTCCCCGGCCAGGGCGCGCCGCTGCTGTGGTTCGAGAACTTCACC
        T   H   P   A   Y   H   G   V   A   E   A   L   T   N   K   T   T   R   G   R
1021    ACCCACCCGGCGTACCACGGCGTCGCCGAGGCCCTGACGAACAAGACCACCCGCGGCCGG
        A   R   R   A   Q   L   R   S   A   *
1081    GCCCGGCGCGCCCAGCTGCGGAGCGCCTAA
```

Fig. 1

```
         M   R   S   Q   A   V   W   A   A   I   L   A   P   A   T   V   S   A   T   L
   1     ATGCGCTCCCAGGCTGTGTGGGCCGCGATACTCGCGCCGGCCACCGTGTCGGCCACGCTC
         N   D   L   A   V   R   A   G   L   K   Y   F   G   T   C   L   S   E   S   Y
  61     AACGACCTCGCCGTCCGGGCCGGGCTCAAGTACTTCGGCACCTGCCTCAGCGAGAGTTAC
         I   N   S   D   S   Q   Y   A   A   L   I   N   D   K   T   E   F   G   G   L
 121     ATCAACAGCGATAGCCAGTATGCGGCCCTCATCAATGACAAGACCGAGTTCGGCGGGCTC
         V   P   E   N   G   M   K   W   D   A   T   E   P   S   Q   G   Q   F   S   F
 181     GTGCCTGAGAACGGCATGAAGTGGGACGCCACCGAGCCCAGCCAGGGCCAGTTCAGCTTC
         S   Q   G   D   I   T   A   N   T   A   K   K   N   G   Q   V   L   R   C   H
 241     AGCCAGGGCGACATCACGGCGAACACGGCCAAGAAGAACGGCCAGGTCCTGCGCTGCCAC
         T   L   V   W   Y   S   Q   L   P   G   W   V   T   S   G   S   W   T   R   S
 301     ACCCTGGTCTGGTACAGCCAGCTTCCAGGATGGGTGACGTCGGGCTCCTGGACCAGGAGC
         T   L   Q   S   V   M   Q   T   H   I   T   N   V   M   G   H   Y   K   G   Q
 361     ACGCTGCAGTCGGTCATGCAGACGCACATCACGAACGTCATGGGCCACTACAAGGGCCAG
         C   Y   A   W   D   V   V   N   E   A   I   A   D   D   G   T   W   R   T   S
 421     TGCTATGCGTGGGACGTGGTGAACGAGGCCATCGCCGACGACGGCACGTGGCGCACCAGC
         V   F   Y   N   T   F   S   T   D   Y   I   P   L   A   F   N   I   A   K   T
 481     GTGTTCTACAACACCTTCTCGACCGACTACATCCCGCTTGCCTTCAACATCGCCAAGACG
         A   D   P   N   A   K   L   Y   Y   N   D   Y   N   L   E   Y   N   G   A   K
 541     GCCGACCCCAACGCCAAGCTGTACTACAACGACTACAACCTCGAGTACAACGGCGCCAAG
         T   D   T   A   V   Q   L   V   Q   L   V   Q   S   A   G   A   P   I   D   G
 601     ACGGACACGGCCGTGCAGCTCGTGCAGCTCGTGCAGTCGGCCGGCGCGCCCATCGACGGC
         V   G   F   Q   G   H   L   I   V   G   S   T   P   G   R   S   S   L   A   T
 661     GTCGGCTTCCAGGGCCACCTGATCGTCGGCAGCACGCCCGGCCGCAGCAGCCTGGCGACC
         A   L   K   R   F   T   A   L   G   L   E   V   A   Y   T   E   L   D   I   R
 721     GCGCTCAAGCGCTTCACCGCCCTCGGCCTGGAGGTGGCCTACACGGAGCTCGACATCCGG
         H   S   S   L   P   P   S   T   S   A   L   A   T   Q   G   N   D   F   A   N
 781     CACTCCAGCCTGCCGCCGTCCACCTCGGCGCTCGCGACGCAGGGCAACGACTTCGCCAAC
         V   V   G   S   C   L   D   V   A   G   C   I   G   V   T   V   W   G   V   T
 841     GTGGTCGGCTCGTGCCTCGACGTCGCCGGCTGCATCGGCGTGACCGTCTGGGGCGTGACC
         D   K   Y   S   W   I   P   Q   T   F   P   G   A   G   D   A   L   L   Y   D
 901     GACAAGTACTCGTGGATCCCGCAGACCTTCCCGGGCGCCGGCGACGCCCTGCTCTACGAC
         D   N   Y   N   K   K   P   A   W   T   S   V   S   S   V   L   A   A   K   A
 961     GACAACTACAACAAGAAGCCCGCCTGGACCTCGGTCTCGTCCGTCCTCGCCGCCAAGGCC
         T   S   P   P   A   S   S   T   T   L   T   T   V   I   T   T   A   P   T
1021     ACCAGCCCGCCCGCCTCGTCGTCCACCACCCTCACCACCGTCATCACCACGGCCCCAACC
         S   T   P   T   S   T   T   A   P   T   T   T   S   S   S   N   G   A   Q   Q
1081     TCCACCCCGACGAGCACCACCGCGCCCACCACCACGTCGTCCTCGAACGGCGCCCAGCAG
         T   H   W   G   Q   C   G   G   I   G   W   T   G   A   T   Q   C   Q   S   P
1141     ACCCACTGGGGCCAGTGCGGTGGCATTGGCTGGACCGGCGCTACGCAGTGCCAGAGCCCG
         Y   T   C   Q   K   L   N   D   W   Y   Y   Q   C   L   *
1201     TACACCTGCCAGAAGCTGAACGACTGGTACTATCAGTGCCTGTAA
```

Fig. 2

SEQUENCE LISTING

<160> NUMBER OF SEQ ID NOS: 6

<210> SEQ ID NO 1
<211> LENGTH: 1110
<212> TYPE: DNA
<213> ORGANISM: Thielavia terrestris

<400> SEQUENCE: 1

```
atgcatctcg cctccgcgtt gctcttcctc gcctcgctgc cctcgggct ggcgggcaag      60
gacaagggca agccgtgcaa gaagggcctc aacacgctcg ccaagcaggc cggcctcaag     120
tacttcggct cggccaccga ctcgccgggc ttccgcgagc gcgccggcta cgaggccgtg     180
tacccgcagt acgaccagat catgtggaag tcgggcgagt tccacatgac gacgcccacc     240
aacggcatga agtgggtctt caccgagccg gagcgcggcg tgttcaactt caccgagggc     300
gagatcgtgg cgtcgctcgc caagcagaac ggcttcatgc tgcgctgcca cgcgctcgtc     360
tggcacagcc agctccccga ctgggtcacg gcgaccaact ggaccgccgc tgaactgcgc     420
cagatcatcg tcaaccacat cacccacgtg gtcggccatt ggaagggcca gtgctatgcc     480
tgggacgtcg ttaacgaggc gctcaacgag gacggcacct accgcgactc catcttctac     540
caggtgctcg gcgaggagta catcaagctg gcctttgaga ctgcctccaa gattgacccg     600
catgccaagc tgtactacaa cgactacaac ctcgagtatc ccggccccaa ggtcaccggc     660
gcccagaaca tcgtcaagat gctcaagacc gctggcatcc gcatcgacgg cgtcggcctg     720
cagtcgcacc tcgtcgccga gagccacccg acgctcgacc agcacatcga cgccatccgg     780
tccttctcca gcctcggcgt cgaggtcgcc ctgaccgagc tcgacgtccg cctgacgctg     840
cccgccaacg cgacgaacct ggccgagcag aacgacgcct acaagaacat cgtcggcgcc     900
tgcgtccagg tccgcggctg catcggcgtc accatctggg acttctacga ccccttcagc     960
tgggtccccg ccaccttccc cggccagggc gcgccgctgc tgtggttcga gaacttcacc    1020
acccacccgg cgtaccacgg cgtcgccgag gccctgacga acaagaccac ccgcggccgg    1080
gcccggcgcg cccagctgcg gagcgcctaa                                     1110
```

<210> SEQ ID NO 2
<211> LENGTH: 369
<212> TYPE: PRT
<213> ORGANISM: Thielavia terrestris

<400> SEQUENCE: 2

```
Met His Leu Ala Ser Ala Leu Leu Phe Leu Ala Ser Leu Pro Leu Gly
1               5                   10                  15
```

Leu Ala Gly Lys Asp Lys Gly Lys Pro Cys Lys Lys Gly Leu Asn Thr
            20                  25                  30

Leu Ala Lys Gln Ala Gly Leu Lys Tyr Phe Gly Ser Ala Thr Asp Ser
        35                  40                  45

Pro Gly Phe Arg Glu Arg Ala Gly Tyr Glu Ala Val Tyr Pro Gln Tyr
    50                  55                  60

Asp Gln Ile Met Trp Lys Ser Gly Glu Phe His Met Thr Thr Pro Thr
65                  70                  75                  80

Asn Gly Met Lys Trp Val Phe Thr Glu Pro Glu Arg Gly Val Phe Asn
                85                  90                  95

Phe Thr Glu Gly Glu Ile Val Ala Ser Leu Ala Lys Gln Asn Gly Phe
            100                 105                 110

Met Leu Arg Cys His Ala Leu Val Trp His Ser Gln Leu Pro Asp Trp
        115                 120                 125

Val Thr Ala Thr Asn Trp Thr Ala Ala Glu Leu Arg Gln Ile Ile Val
    130                 135                 140

Asn His Ile Thr His Val Val Gly His Trp Lys Gly Gln Cys Tyr Ala
145                 150                 155                 160

Trp Asp Val Val Asn Glu Ala Leu Asn Glu Asp Gly Thr Tyr Arg Asp
                165                 170                 175

Ser Ile Phe Tyr Gln Val Leu Gly Glu Tyr Ile Lys Leu Ala Phe
            180                 185                 190

Glu Thr Ala Ser Lys Ile Asp Pro His Ala Lys Leu Tyr Tyr Asn Asp
        195                 200                 205

Tyr Asn Leu Glu Tyr Pro Gly Pro Lys Val Thr Gly Ala Gln Asn Ile
    210                 215                 220

Val Lys Met Leu Lys Thr Ala Gly Ile Arg Ile Asp Gly Val Gly Leu
225                 230                 235                 240

Gln Ser His Leu Val Ala Glu Ser His Pro Thr Leu Asp Gln His Ile
                245                 250                 255

Asp Ala Ile Arg Ser Phe Ser Ser Leu Gly Val Glu Val Ala Leu Thr
            260                 265                 270

Glu Leu Asp Val Arg Leu Thr Leu Pro Ala Asn Ala Thr Asn Leu Ala
        275                 280                 285

Glu Gln Asn Asp Ala Tyr Lys Asn Ile Val Gly Ala Cys Val Gln Val
    290                 295                 300

Arg Gly Cys Ile Gly Val Thr Ile Trp Asp Phe Tyr Asp Pro Phe Ser
305                 310                 315                 320

Trp Val Pro Ala Thr Phe Pro Gly Gln Gly Ala Pro Leu Leu Trp Phe
                325                 330                 335

Glu Asn Phe Thr Thr His Pro Ala Tyr His Gly Val Ala Glu Ala Leu
            340                 345                 350

Thr Asn Lys Thr Thr Arg Gly Arg Ala Arg Arg Ala Gln Leu Arg Ser
        355                 360                 365

Ala

<210> SEQ ID NO 3
<211> LENGTH: 1245
<212> TYPE: DNA
<213> ORGANISM: Thielavia terrestris

<400> SEQUENCE: 3
atgcgctccc aggctgtgtg ggccgcgata ctcgcgccgg ccaccgtgtc ggccacgctc      60

-continued

```
aacgacctcg ccgtccgggc cgggctcaag tacttcggca cctgcctcag cgagagttac      120
atcaacagcg atagccagta tgcggccctc atcaatgaca agaccgagtt cggcgggctc      180
gtgcctgaga acggcatgaa gtgggacgcc accgagccca gccagggcca gttcagcttc      240
agccagggcg acatcacggc gaacacggcc aagaagaacg gccaggtcct gcgctgccac      300
accctggtct ggtacagcca gcttccagga tgggtgacgt cgggctcctg gaccaggagc      360
acgctgcagt cggtcatgca gacgcacatc acgaacgtca tgggccacta caagggccag      420
tgctatgcgt gggacgtggt gaacgaggcc atcgccgacg acggcacgtg gcgcaccagc      480
gtgttctaca acaccttctc gaccgactac atcccgcttg ccttcaacat cgccaagacg      540
gccgacccca cgccaagct gtactacaac gactacaacc tcgagtacaa cggcgccaag      600
acggacacgg ccgtgcagct cgtgcagctc gtgcagtcgg ccggcgcgcc catcgacggc      660
gtcggcttcc agggccacct gatcgtcggc agcacgcccg gccgcagcag cctggcgacc      720
gcgctcaagc gcttcaccgc cctcggcctg gaggtggcct acacggagct cgacatccgg      780
cactccagcc tgccgccgtc cacctcggcg ctcgcgacgc agggcaacga cttcgccaac      840
gtggtcggct cgtgcctcga cgtcgccggc tgcatcggcg tgaccgtctg gggcgtgacc      900
gacaagtact cgtggatccc gcagaccttc ccgggcgccg cgacgccct gctctacgac      960
gacaactaca caagaagcc cgcctggacc tcggtctcgt ccgtcctcgc cgccaaggcc     1020
accagcccgc cgcctcgtc gtccaccacc ctcaccaccg tcatcaccac ggccccaacc     1080
tccaccccga cgagcaccac cgcgcccacc accacgtcgt cctcgaacgg cgcccagcag     1140
acccactggg gccagtgcgg tggcattggc tggaccggcg ctacgcagtg ccagagcccg     1200
tacacctgcc agaagctgaa cgactggtac tatcagtgcc tgtaa                      1245
```

<210> SEQ ID NO 4
<211> LENGTH: 414
<212> TYPE: PRT
<213> ORGANISM: Thielavia terrestris

<400> SEQUENCE: 4

```
Met Arg Ser Gln Ala Val Trp Ala Ala Ile Leu Ala Pro Ala Thr Val
1               5                   10                  15

Ser Ala Thr Leu Asn Asp Leu Ala Val Arg Ala Gly Leu Lys Tyr Phe
                20                  25                  30

Gly Thr Cys Leu Ser Glu Ser Tyr Ile Asn Ser Asp Ser Gln Tyr Ala
            35                  40                  45

Ala Leu Ile Asn Asp Lys Thr Glu Phe Gly Gly Leu Val Pro Glu Asn
        50                  55                  60

Gly Met Lys Trp Asp Ala Thr Glu Pro Ser Gln Gly Gln Phe Ser Phe
65                  70                  75                  80

Ser Gln Gly Asp Ile Thr Ala Asn Thr Ala Lys Lys Asn Gly Gln Val
                85                  90                  95

Leu Arg Cys His Thr Leu Val Trp Tyr Ser Gln Leu Pro Gly Trp Val
            100                 105                 110

Thr Ser Gly Ser Trp Thr Arg Ser Thr Leu Gln Ser Val Met Gln Thr
        115                 120                 125

His Ile Thr Asn Val Met Gly His Tyr Lys Gly Gln Cys Tyr Ala Trp
    130                 135                 140

Asp Val Val Asn Glu Ala Ile Ala Asp Asp Gly Thr Trp Arg Thr Ser
145                 150                 155                 160

Val Phe Tyr Asn Thr Phe Ser Thr Asp Tyr Ile Pro Leu Ala Phe Asn
```

-continued

```
                165                 170                 175

Ile Ala Lys Thr Ala Asp Pro Asn Ala Lys Leu Tyr Tyr Asn Asp Tyr
            180                 185                 190

Asn Leu Glu Tyr Asn Gly Ala Lys Thr Asp Thr Ala Val Gln Leu Val
        195                 200                 205

Gln Leu Val Gln Ser Ala Gly Ala Pro Ile Asp Gly Val Gly Phe Gln
    210                 215                 220

Gly His Leu Ile Val Gly Ser Thr Pro Gly Arg Ser Ser Leu Ala Thr
225                 230                 235                 240

Ala Leu Lys Arg Phe Thr Ala Leu Gly Leu Glu Val Ala Tyr Thr Glu
                245                 250                 255

Leu Asp Ile Arg His Ser Ser Leu Pro Pro Ser Thr Ser Ala Leu Ala
            260                 265                 270

Thr Gln Gly Asn Asp Phe Ala Asn Val Val Gly Ser Cys Leu Asp Val
        275                 280                 285

Ala Gly Cys Ile Gly Val Thr Val Trp Gly Val Thr Asp Lys Tyr Ser
    290                 295                 300

Trp Ile Pro Gln Thr Phe Pro Gly Ala Gly Asp Ala Leu Leu Tyr Asp
305                 310                 315                 320

Asp Asn Tyr Asn Lys Lys Pro Ala Trp Thr Ser Val Ser Ser Val Leu
                325                 330                 335

Ala Ala Lys Ala Thr Ser Pro Pro Ala Ser Ser Ser Thr Thr Leu Thr
            340                 345                 350

Thr Val Ile Thr Thr Ala Pro Thr Ser Thr Pro Thr Ser Thr Thr Ala
        355                 360                 365

Pro Thr Thr Thr Ser Ser Ser Asn Gly Ala Gln Gln Thr His Trp Gly
    370                 375                 380

Gln Cys Gly Gly Ile Gly Trp Thr Gly Ala Thr Gln Cys Gln Ser Pro
385                 390                 395                 400

Tyr Thr Cys Gln Lys Leu Asn Asp Trp Tyr Tyr Gln Cys Leu
                405                 410

<210> SEQ ID NO 5
<211> LENGTH: 16
<212> TYPE: DNA
<213> ORGANISM: Thielavia terrestris

<400> SEQUENCE: 5
gtaaaacgac ggccag                                                      16

<210> SEQ ID NO 6
<211> LENGTH: 25
<212> TYPE: DNA
<213> ORGANISM: Thielavia terrestris
<220> FEATURE:
<221> NAME/KEY: misc_feature
<222> LOCATION: (24)..(24)
<223> OTHER INFORMATION: V = A, C, OR G
<220> FEATURE:
<221> NAME/KEY: misc_feature
<222> LOCATION: (25)..(25)
<223> OTHER INFORMATION: N= A, C, G, OR T

<400> SEQUENCE: 6 ttttttttt ttttttttt tttvn                                              25
```

POLYPEPTIDES HAVING XYLANASE ACTIVITY AND POLYNUCLEOTIDES ENCODING SAME

CROSS-REFERENCE TO RELATED APPLICATIONS

This application is a divisional application of U.S. patent application Ser. No. 14/605,764, filed Jan. 26, 2015, now U.S. Pat. No. 9,353,360, which is a divisional application of U.S. patent application Ser. No. 12/941,474, filed Nov. 8, 2010, now U.S. Pat. No. 8,940,515, which is a divisional application of U.S. patent application Ser. No. 12/327,439, filed Dec. 3, 2008, now U.S. Pat. No. 7,851,193, which claims the benefit of U.S. Provisional Application No. 60/992,565, filed Dec. 5, 2007, which applications are incorporated herein by reference.

STATEMENT AS TO RIGHTS TO INVENTIONS MADE UNDER FEDERALLY SPONSORED RESEARCH AND DEVELOPMENT

This invention was made with Government support under NREL Subcontract No. ZCO-30017-02, Prime Contract DE-AC36-98GO10337 awarded by the Department of Energy. The government has certain rights in this invention.

REFERENCE TO A SEQUENCE LISTING

This application contains a Sequence Listing in computer readable form. The computer readable form is incorporated herein by reference.

REFERENCE TO DEPOSITS OF BIOLOGICAL MATERIAL

This application contains a reference to deposits of biological material, which deposits are incorporated herein by reference.

BACKGROUND OF THE INVENTION

Field of the Invention

The present invention relates to isolated polypeptides having xylanase activity and isolated polynucleotides encoding the polypeptides. The invention also relates to nucleic acid constructs, vectors, and host cells comprising the polynucleotides as well as methods of producing and using the polypeptides.

Description of the Related Art

Plant cell wall polysaccharides constitute approximately 90% of the plant cell wall and can be divided into three groups: cellulose, hemicellulose, and pectin. Cellulose represents the major constituent of call wall polysaccharides. Hemicelluloses are the second most abundant constituent of plant cell walls. The major hemicellulose polymer is xylan. The structure of xylans found in cell walls of plants can differ significantly depending on their origin, but they always contain a beta-1,4-linked D-xylose backbone. The beta-1,4-linked D-xylose backbone can be substituted by various side groups, such as L-aribinose, D-galactose, acetyl, feruloyl, p-coumaroyl, and glucuronic acid residues.

The biodegradation of the xylan backbone depends on two classes of enzymes: endoxylanases and beta-xylosidases. Endoxylanases (EC 3.2.1.8) cleave the xylan backbone into smaller oligosaccharides, which can be further degraded to xylose by beta-xylosidases (EC 3.2.1.37). Other enzymes involved in the degradation of xylan include, for example, acetylxylan esterase, arabinase, alpha-glucuronidase, ferulic acid esterase, and p-coumaric acid esterase.

Merchant et al., 1988, *Biotechnology Letters* 10: 513-516, describe the production of xylanase by *Thielavia terrestris*. Gilbert et al., 1993, *Applied Microbiology and Biotechnology* 40: 508-514, disclose a comparison of two xylanases from *Thielavia terrestris* and *Thermoascus crustaceus*. WO 1997/027293 discloses an enzyme from *Thielavia terrestris* exhibiting xylanase activity.

The present invention relates to polypeptides having xylanase activity and polynucleotides encoding the polypeptides.

SUMMARY OF THE INVENTION

The present invention relates to isolated polypeptides having xylanase activity selected from the group consisting of:

(a) a polypeptide comprising an amino acid sequence having at least 60% identity to the mature polypeptide of SEQ ID NO: 4 or at least 80% identity to the mature polypeptide of SEQ ID NO: 2;

(b) a polypeptide encoded by a polynucleotide that hybridizes under at least medium-high stringency conditions with (i) the mature polypeptide coding sequence of SEQ ID NO: 3, (ii) the genomic DNA sequence comprising the mature polypeptide coding sequence of SEQ ID NO: 3, or (iii) a full-length complementary strand of (i) or (ii), or under at least high stringency conditions with (iv) the mature polypeptide coding sequence of SEQ ID NO: 1, (v) the genomic DNA sequence comprising the mature polypeptide coding sequence of SEQ ID NO: 1, or (vi) a full-length complementary strand of (iv) or (v);

(c) a polypeptide encoded by a polynucleotide comprising a nucleotide sequence having at least 60% identity to the mature polypeptide coding sequence of SEQ ID NO: 3 or at least 80% identity to the mature polypeptide coding sequence of SEQ ID NO: 1; and (d) a variant comprising a substitution, deletion, and/or insertion of one or more (several) amino acids of the mature polypeptide of SEQ ID NO: 2 or SEQ ID NO: 4.

The present invention also relates to isolated polynucleotides encoding polypeptides having xylanase activity, selected from the group consisting of:

(a) a polynucleotide encoding a polypeptide comprising an amino acid sequence having at least 60% identity to the mature polypeptide of SEQ ID NO: 4 or at least 80% identity to the mature polypeptide of SEQ ID NO: 2;

(b) a polynucleotide that hybridizes under at least medium-high stringency conditions with (i) the mature polypeptide coding sequence of SEQ ID NO: 3, (ii) the genomic DNA sequence comprising the mature polypeptide coding sequence of SEQ ID NO: 3, or (iii) a full-length complementary strand of (i) or (ii), or at least high stringency conditions with (iv) the mature polypeptide coding sequence of SEQ ID NO: 1, (v) the genomic DNA sequence comprising the mature polypeptide coding sequence of SEQ ID NO: 1, or (vi) a full-length complementary strand of (iv) or (v);

(c) a polynucleotide comprising a nucleotide sequence having at least 60% identity to the mature polypeptide coding sequence of SEQ ID NO: 3 or at least 80% identity to the mature polypeptide coding sequence of SEQ ID NO: 1; and (d) a polynucleotide encoding a variant comprising a substitution, deletion, and/or insertion of one or more (several) amino acids of the mature polypeptide of SEQ ID NO: 2 or SEQ ID NO: 4.

The present invention also relates to nucleic acid constructs, recombinant expression vectors, recombinant host cells comprising the polynucleotides, and methods of producing a polypeptide having xylanase activity.

The present invention also relates to methods of inhibiting the expression of a polypeptide having xylanase activity in a cell, comprising administering to the cell or expressing in the cell a double-stranded RNA (dsRNA) molecule, wherein the dsRNA comprises a subsequence of a polynucleotide of the present invention. The present also relates to a double-stranded inhibitory RNA (dsRNA) molecule, wherein optionally the dsRNA is a siRNA or a miRNA molecule.

The present invention also relates to methods for degrading a xylan-containing material with a polypeptide having xylanase activity.

The present invention also relates to plants comprising an isolated polynucleotide encoding a polypeptide having xylanase activity.

The present invention also relates to methods of producing a polypeptide having xylanase, comprising: (a) cultivating a transgenic plant or a plant cell comprising a polynucleotide encoding the polypeptide having xylanase activity under conditions conducive for production of the polypeptide; and (b) recovering the polypeptide.

The present invention further relates to nucleic acid constructs comprising a gene encoding a protein, wherein the gene is operably linked to a nucleotide sequence encoding a signal peptide comprising or consisting of amino acids 1 to 19 of SEQ ID NO: 2 or amino acids 1 to 18 of SEQ ID NO: 4, wherein the gene is foreign to the nucleotide sequence.

BRIEF DESCRIPTION OF THE FIGURES

FIG. 1 shows the cDNA sequence and the deduced amino acid sequence of a *Thielavia terrestris* NRRL 8126 GH10A xylanase (SEQ ID NOs: 1 and 2, respectively).

FIG. 2 shows the cDNA sequence and the deduced amino acid sequence of a *Thielavia terrestris* NRRL 8126 GH10B xylanase (SEQ ID NOs: 3 and 4, respectively).

DEFINITIONS

Figure 3:
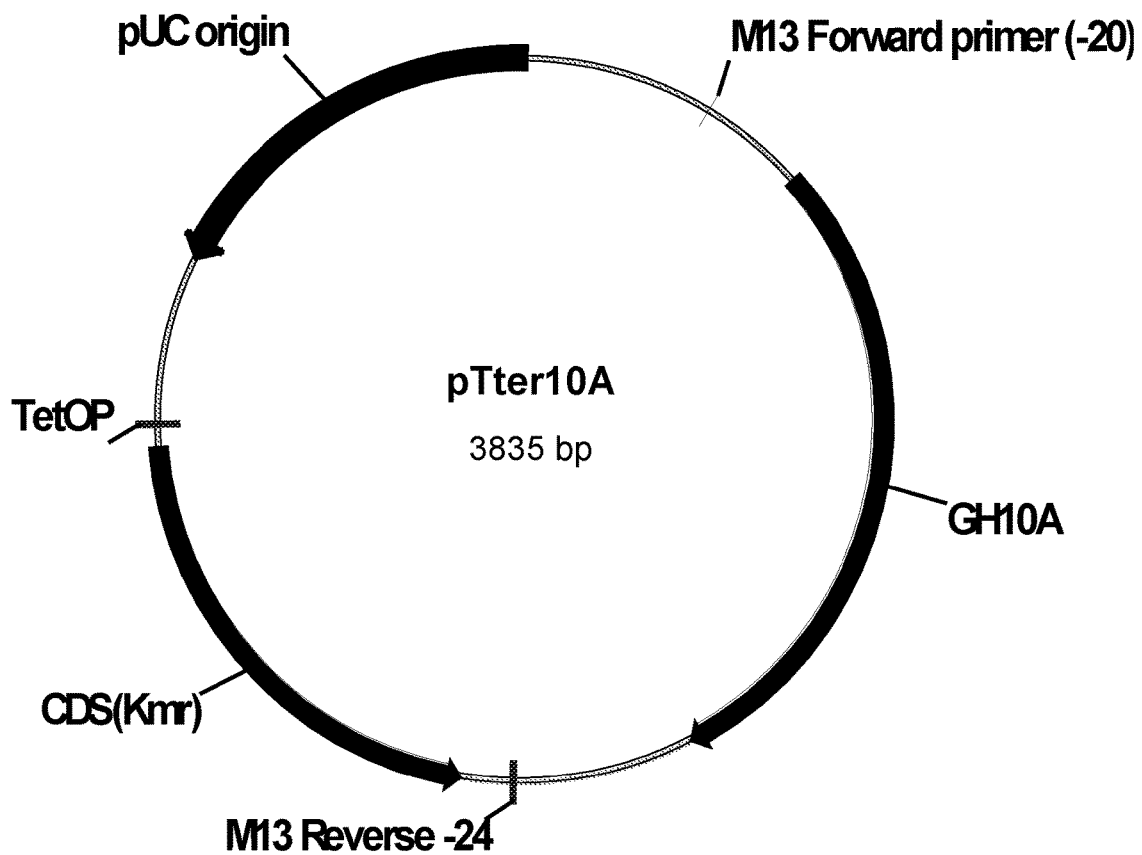
FIG. 3 shows a restriction map of pTter10A.

Xylanase activity: The term "xylanase activity" is defined herein as a 1,4-beta-D-xylan-xylanohydrolase activity (E.C. 3.2.1.8) that catalyzes the endohydrolysis of 1,4-beta-D-xylosidic linkages in xylans. For purposes of the present invention, xylanase activity is determined using 0.2% AZCL-arabinoxylan as substrate in 0.01% Triton X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the xylanase activity of the mature polypeptide of SEQ ID NO: 2 or SEQ ID NO: 4.

Family 10 or Family GH10 or GH10: The term "Family 10" or "Family GH10" or "GH10" is defined herein as a polypeptide falling into the glycoside hydrolase Family 10 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

Xylan-containing material: The term "xylan-containing material" is defined herein as any material comprising xylan as a constituent. Xylan is a plant cell wall polysaccharide containing a backbone of beta-1,4-linked xylose residues. Side chains of 4-O-methylglucuronic acid and arabinose are generally present in varying amounts, together with acetyl and feruloyl groups. Xylan is a major constituent of hemicellulose.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide in its final form following translation and any post-translational modifications, such as N-terminal processing, C-terminal truncation, glycosylation, phosphorylation, etc. In a preferred aspect, the mature polypeptide is amino acids 20 to 369 of SEQ ID NO: 2 based on the SignalP software program (Nielsen et al., 1997, *Protein Engineering* 10: 1-6) that predicts amino acids 1 to 19 of SEQ ID NO: 2 are a signal peptide. In another preferred aspect, the mature polypeptide is amino acids 19 to 414 of SEQ ID NO: 4 based on the SignalP software program that predicts amino acids 1 to 18 of SEQ ID NO: 4 are a signal peptide.

Mature polypeptide coding sequence: The term "mature polypeptide coding sequence" is defined herein as a nucleotide sequence that encodes a mature polypeptide having xylanase activity. In a preferred aspect, the mature polypeptide coding sequence is nucleotides 58 to 1107 of SEQ ID NO: 1 based on the SignalP software program that predicts nucleotides 1 to 57 encode a signal peptide. In another preferred aspect, the mature polypeptide coding sequence is nucleotides 55 to 1242 of SEQ ID NO: 3 based on the SignalP software program that predicts nucleotides 1 to 54 encode a signal peptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment−Total Number of Gaps in Alignment)

Homologous sequence: The term "homologous sequence" is defined herein as a predicted protein that has an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Thielavia terrestris* xylanase of SEQ ID NO: 2 or SEQ ID NO: 4; or the mature polypeptides thereof.

Polypeptide fragment: The term "polypeptide fragment" is defined herein as a polypeptide having one or more (several) amino acids deleted from the amino and/or carboxyl terminus of the mature polypeptide of SEQ ID NO: 2 or SEQ ID NO: 4; or a homologous sequence thereof; wherein the fragment has xylanase activity. In a preferred aspect, a fragment contains at least 305 amino acid residues, more preferably at least 320 amino acid residues, and most preferably at least 335 amino acid residues, of the mature polypeptide of SEQ ID NO: 2 or a homologous sequence thereof. In another preferred aspect, a fragment contains at least 340 amino acid residues, more preferably at least 360 amino acid residues, and most preferably at least 380 amino acid residues, of the mature polypeptide of SEQ ID NO: 4 or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO: 1 or SEQ ID NO: 3; or a homologous sequence thereof; wherein the subsequence encodes a polypeptide fragment having xylanase activity. In a preferred aspect, a subsequence contains at least 915 nucleotides, more preferably at least 960 nucleotides, and most preferably at least 1005 nucleotides of the mature polypeptide coding sequence of SEQ ID NO: 1 or a homologous sequence thereof. In another preferred aspect, a subsequence contains at least 1020 nucleotides, more preferably at least 1080 nucleotides, and most preferably at least 1140 nucleotides of the mature polypeptide coding sequence of SEQ ID NO: 3 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2 or SEQ ID NO: 4; or a homologous sequence thereof; as well as genetic manipulation of the DNA encoding such a polypeptide. The modification can be a substitution, a deletion, and/or an insertion of one or more (several) amino acids as well as replacements of one or more (several) amino acid side chains.

Artificial variant: When used herein, the term "artificial variant" means a polypeptide having xylanase activity produced by an organism expressing a modified polynucleotide sequence of the mature polypeptide coding sequence of SEQ ID NO: 1 or SEQ ID NO: 3; or a homologous sequence thereof. The modified nucleotide sequence is obtained through human intervention by modification of the polynucleotide sequence disclosed in SEQ ID NO: 1 or SEQ ID NO: 3; or a homologous sequence thereof.

DETAILED DESCRIPTION OF THE INVENTION

Polypeptides Having Xylanase Activity

In a first aspect, the present invention relates to isolated polypeptides comprising an amino acid sequence having a degree of identity to the mature polypeptide of SEQ ID NO: 2 or SEQ ID NO: 4 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have xylanase activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2 or SEQ ID NO: 4.

A polypeptide of the present invention preferably comprises the amino acid sequence of SEQ ID NO: 2 or SEQ ID NO: 4 or an allelic variant thereof; or a fragment thereof having xylanase activity.

In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 20 to 369 of SEQ ID NO: 2, or an allelic variant thereof; or a fragment thereof having xylanase activity. In another preferred aspect, the polypeptide comprises amino acids 20 to 369 of SEQ ID NO: 2. In another preferred aspect, the polypeptide consists of the amino acid sequence of SEQ ID NO: 2 or an allelic variant thereof; or a fragment thereof having xylanase activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 20 to 369 of SEQ ID NO: 2 or an allelic variant thereof; or a fragment thereof having xylanase activity. In another preferred aspect, the polypeptide consists of amino acids 20 to 369 of SEQ ID NO: 2.

In another preferred aspect, the polypeptide comprises the amino acid sequence of SEQ ID NO: 4. In another preferred aspect, the polypeptide comprises the mature polypeptide of SEQ ID NO: 4. In another preferred aspect, the polypeptide comprises amino acids 19 to 414 of SEQ ID NO: 4, or an allelic variant thereof; or a fragment thereof having xylanase activity. In another preferred aspect, the polypeptide comprises amino acids 19 to 414 of SEQ ID NO: 4. In another preferred aspect, the polypeptide consists of the amino acid sequence of SEQ ID NO: 4 or an allelic variant thereof; or a fragment thereof having xylanase activity. In another preferred aspect, the polypeptide consists of the amino acid sequence of SEQ ID NO: 4. In another preferred aspect, the polypeptide consists of the mature polypeptide of SEQ ID NO: 4. In another preferred aspect, the polypeptide consists of amino acids 19 to 414 of SEQ ID NO: 4 or an allelic variant thereof; or a fragment thereof having xylanase activity. In another preferred aspect, the polypeptide consists of amino acids 19 to 414 of SEQ ID NO: 4.

In a second aspect, the present invention relates to isolated polypeptides having xylanase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1 or SEQ ID NO: 3, (ii) the genomic DNA sequence comprising the mature polypeptide coding sequence of SEQ ID NO: 1 or SEQ ID NO: 3, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of the mature polypeptide coding sequence of SEQ ID NO: 1 or SEQ ID NO: 3 contains at least 100 contiguous nucleotides or preferably at least 200 contiguous nucleotides. Moreover, the subsequence may encode a polypeptide fragment having xylanase activity. In a preferred aspect, the complementary strand is the full-length complementary strand of the mature polypeptide coding sequence of SEQ ID NO: 1 or SEQ ID NO: 3.

The nucleotide sequence of SEQ ID NO: 1 or SEQ ID NO: 3; or a subsequence thereof; as well as the amino acid sequence of SEQ ID NO: 2 or SEQ ID NO: 4; or a fragment thereof; may be used to design nucleic acid probes to identify and clone DNA encoding polypeptides having xylanase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having xylanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or SEQ ID NO: 3; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1 or SEQ ID NO: 3; the genomic DNA sequence comprising the mature polypeptide coding sequence of SEQ ID NO: 1 or SEQ ID NO: 3; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 58 to 1107 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pTter10A which is contained in *E. coli* NRRL B-50079, wherein the polynucleotide sequence thereof encodes a polypeptide having xylanase activity. In another preferred aspect, the nucleic acid probe is the mature polypeptide coding region contained in plasmid pTter10A which is contained in *E. coli* NRRL B-50079.

In another preferred aspect, the nucleic acid probe is the mature polypeptide coding sequence of SEQ ID NO: 3. In another preferred aspect, the nucleic acid probe is nucleotides 55 to 1242 of SEQ ID NO: 3. In another preferred aspect, the nucleic acid probe is a polynucleotide sequence that encodes the polypeptide of SEQ ID NO: 4, or a subsequence thereof. In another preferred aspect, the nucleic acid probe is SEQ ID NO: 3. In another preferred aspect, the nucleic acid probe is the polynucleotide sequence contained in plasmid pTter10B which is contained in *E. coli* NRRL B-50080, wherein the polynucleotide sequence thereof encodes a polypeptide having xylanase activity. In another preferred aspect, the nucleic acid probe is the mature polypeptide coding region contained in plasmid pTter10B which is contained in *E. coli* NRRL B-50080.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having xylanase activity encoded by polynucleotides comprising or consisting of nucleotide sequences that have a degree of identity to the mature polypeptide coding sequence of SEQ ID NO: 1 or SEQ ID NO: 3 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a polypeptide having xylanase activity. See polynucleotide section herein.

In a fourth aspect, the present invention relates to artificial variants comprising a substitution, deletion, and/or insertion of one or more (or several) amino acids of the mature polypeptide of SEQ ID NO: 2 or SEQ ID NO: 4; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for biological activity (i.e., xylanase activity) to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2 or SEQ ID NO: 4, such as amino acids 20 to 369 of SEQ ID NO: 2 or amino acids 17 to 413 of SEQ ID NO:4, is 10, preferably 9, more preferably 8, more preferably 7, more preferably at most 6, more preferably 5, more preferably 4, even more preferably 3, most preferably 2, and even most preferably 1.

Sources of Polypeptides Having Xylanase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having xylanase activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having xylanase activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having xylanase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having xylanase activity.

In another preferred aspect, the polypeptide is a *Streptococcus equisimilis, Streptococcus pyogenes, Streptococcus uberis*, or *Streptococcus equi* subsp. *Zooepidemicus* polypeptide having xylanase activity.

In another preferred aspect, the polypeptide is a *Streptomyces achromogenes, Streptomyces avermitilis, Streptomyces coelicolor, Streptomyces griseus*, or *Streptomyces lividans* polypeptide having xylanase activity.

A polypeptide having xylanase activity of the present invention may also be a fungal polypeptide, and more preferably a yeast polypeptide such as a *Candida, Kluyveromyces, Pichia, Saccharomyces, Schizosaccharomyces*, or *Yarrowia* polypeptide having xylanase activity; or more preferably a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having xylanase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having xylanase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Trichoderma harzianum, Trichoderma koningii, Trichoderma longibrachiatum, Trichoderma reesei*, or *Trichoderma viride* polypeptide having xylanase activity.

In another preferred aspect, the polypeptide is a *Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila*, or *Thielavia terrestris* polypeptide having xylanase activity.

In a more preferred aspect, the polypeptide is a *Thielavia terrestris* polypeptide having xylanase activity. In a most preferred aspect, the polypeptide is a *Thielavia terrestris* NRRL 8126 polypeptide having xylanase activity, e.g., the polypeptide comprising the mature polypeptide of SEQ ID NO: 2 or SEQ ID NO: 4.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having xylanase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr- Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having xylanase activity of the present invention.

In a preferred aspect, the nucleotide sequence comprises or consists of SEQ ID NO: 1. In another more preferred aspect, the nucleotide sequence comprises or consists of the sequence contained in plasmid pTter10A which is contained in *E. coli* NRRL B-50079. In another preferred aspect, the nucleotide sequence comprises or consists of the mature polypeptide coding sequence of SEQ ID NO: 1. In another preferred aspect, the nucleotide sequence comprises or consists of nucleotides 58 to 1107 of SEQ ID NO: 1. In another more preferred aspect, the nucleotide sequence comprises or consists of the mature polypeptide coding sequence contained in plasmid pTter10A which is contained in *E. coli* NRRL B-50079. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 that have xylanase activity.

In another preferred aspect, the nucleotide sequence comprises or consists of SEQ ID NO: 3. In another more preferred aspect, the nucleotide sequence comprises or consists of the sequence contained in plasmid pTter10B which is contained in *E. coli* NRRL B-50080. In another preferred aspect, the nucleotide sequence comprises or consists of the mature polypeptide coding sequence of SEQ ID NO: 3. In another preferred aspect, the nucleotide sequence comprises or consists of nucleotides 55 to 1242 of SEQ ID NO: 3. In another more preferred aspect, the nucleotide sequence comprises or consists of the mature polypeptide coding sequence contained in plasmid pTter10B which is contained in *E. coli* NRRL B-50080. The present invention also encompasses nucleotide sequences that encode polypeptides comprising or consisting of the amino acid sequence of SEQ ID NO: 4 or the mature polypeptide thereof, which differ from SEQ ID NO: 3 or the mature polypeptide coding sequence thereof by virtue of the degeneracy of the genetic code. The present invention also relates to subsequences of SEQ ID NO: 3 that encode fragments of SEQ ID NO: 4 that have xylanase activity.

The present invention also relates to mutant polynucleotides comprising or consisting of at least one mutation in the mature polypeptide coding sequence of SEQ ID NO: 1 and SEQ ID NO: 3, in which the mutant nucleotide sequence encodes the mature polypeptide of SEQ ID NO: 2 and SEQ ID NO: 4, respectively.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Thielavia*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1 or SEQ ID NO: 3 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1 or SEQ ID NO: 3, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for xylanase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1 or SEQ ID NO: 3, (ii) the genomic DNA sequence comprising the mature polypeptide coding sequence of SEQ ID NO: 1 or SEQ ID NO: 3, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO: 1 or SEQ ID NO: 3.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1 or SEQ ID NO: 3, (ii) the genomic DNA sequence comprising the mature polypeptide coding sequence of SEQ ID NO: 1 or SEQ ID NO: 3, or (iii) a full-length complementary strand of (i) or (ii); and (b) isolating the hybridizing polynucleotide, which encodes a polypeptide having xylanase activity. In a preferred aspect, the complementary strand is the full-length complementary strand of the mature polypeptide coding sequence of SEQ ID NO: 1 or SEQ ID NO: 3.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 19 of SEQ ID NO: 2. In another preferred aspect, the signal peptide coding sequence comprises or consists of nucleotides 1 to 57 of SEQ ID NO: 1. In another preferred aspect, the signal peptide comprises or consists of amino acids 1 to 18 of SEQ ID NO: 4. In another preferred aspect, the signal peptide coding sequence comprises or consists of nucleotides 1 to 54 of SEQ ID NO: 3.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAM111 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but are not limited to, *Bacillus*, *Streptococcus*, *Streptomyces*, *Staphylococcus*, *Enterococcus*, *Lactobacillus*, *Lactococcus*, *Clostridium*, *Geobacillus*, and *Oceanobacillus*. Gram negative bacteria include, but are not limited to, *E. coli*, *Pseudomonas*, *Salmonella*, *Campylobacter*, *Helicobacter*, *Flavobacterium*, *Fusobacterium*, *Ilyobacter*, *Neisseria*, and *Ureaplasma*.

The bacterial host cell may be any *Bacillus* cell. *Bacillus* cells useful in the practice of the present invention include, but are not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

In a preferred aspect, the bacterial host cell is a *Bacillus amyloliquefaciens*, *Bacillus lentus*, *Bacillus licheniformis*, *Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (*Praha*) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrys-* osporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238 023 and Yelton et al., 1984, Proceedings of the National Academy of Sciences USA 81: 1470-1474. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods of producing a polypeptide having xylanase activity of the present invention, comprising: (a) cultivating a cell, which in its wild-type form produces the polypeptide, under conditions conducive for production of the polypeptide; and (b) recovering the polypeptide. In a preferred aspect, the cell is of the genus Thielavia. In a more preferred aspect, the cell is Thielavia terrestris. In a most preferred aspect, the cell is Thielavia terrestris NRRL 8126.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1 or SEQ ID NO: 3, wherein the mutant nucleotide sequence encodes a polypeptide that comprises or consists of the mature polypeptide of SEQ ID NO: 2 or SEQ ID NO: 4, respectively, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having xylanase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism Arabidopsis thaliana.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having xylanase activity of the present invention under conditions conducive for production of the polypeptide; and (b) recovering the polypeptide.

Removal or Reduction of Xylanase Activity

The present invention also relates to methods of producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of xylanase activity by fermentation of a cell that produces both a polypeptide of the present invention as well as the protein product of interest by adding an effective amount of an agent capable of inhibiting xylanase activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of xylanase activity by cultivating the cell under conditions permitting the expression of the product, subjecting the resultant culture broth to a combined pH and temperature treatment so as to reduce the xylanase activity substantially, and recovering the product from the culture broth. Alternatively, the combined pH and temperature treatment may be performed on an enzyme preparation recovered from the culture broth. The combined pH and temperature treatment may optionally be used in combination with a treatment with an xylanase inhibitor.

In accordance with this aspect of the invention, it is possible to remove at least 60%, preferably at least 75%, more preferably at least 85%, still more preferably at least 95%, and most preferably at least 99% of the xylanase activity. Complete removal of xylanase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially xylanase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulolytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The xylanase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from xylanase activity that is produced by a method of the present invention.

Methods of Inhibiting Expression of a Polypeptide Having Xylanase Activity

The present invention also relates to methods of inhibiting the expression of a polypeptide having xylanase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (sRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1 or SEQ ID NO: 3 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing therapeutics. In one aspect, the invention provides methods to selectively degrade RNA using the dsRNAis of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. No. 6,506,559; U.S. Pat. No. 6,511,824; U.S. Pat. No. 6,515,109; and U.S. Pat. No. 6,489,127.

Compositions

The present invention also relates to compositions comprising a polypeptide of the present invention. Preferably, the compositions are enriched in such a polypeptide. The term "enriched" indicates that the xylanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium suiphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having xylanase activity.

The polypeptides of the present invention can be used for degradation or modification of plant cell walls or any xylan-containing material originating from plant cells walls. Examples of various uses are described below (see, WO 2002/18561, for other uses). The dosage of the polypeptides of the present invention and other conditions under which the preparation is used may be determined on the basis of methods known in the art.

The enzymatic degradation of xylan is facilitated by full or partial removal of the side branches. The polypeptides of the present invention are preferably used in conjunction with other xylan degrading enzymes such as acetylxylan esterases, arabinofuranosidases, xylosidases, feruloyl esterases, glucuronidases, and a combination thereof, in processes wherein xylan is to be degraded. For example, acetyl groups can be removed by acetylxylan esterases; arabinose groups by alpha-arabinosidases; feruloyl groups by feruloyl esterases, and glucuronic acid groups by alpha-glucuronidases. The oligomers released by the xylanases, or by a combination of xylanases and side branch-hydrolyzing enzymes, can be further degraded to free xylose by beta-xylosidases. A polypeptide of the present invention is preferably a component of a composition comprising one or more (several) xylan degrading enzymes. In the various uses described below, a polypeptide of the present invention is preferably used in combination with one or more (several) xylan degrading enzymes.

Consequently, the present invention also relates to methods for degrading a xylan-containing material, comprising treating the xylan-containing material with such a polypeptide having xylanase activity. In a preferred aspect, the xylan-containing material is further treated with a xylan degrading enzyme. The xylan degrading enzyme can be selected from the group consisting of a an acetyxylan esterase, a feruloyl esterase, an arabinofuranosidase, a xylosidase, a glucuronidase, and a combination thereof.

The plant material may be degraded in order to improve different kinds of processing, facilitate purification or extraction of components other than the xylans, like purification of beta-glucan or beta-glucan oligomers from cereals, improve the feed value, decrease the water binding capacity, improve the degradability in waste water plants, improve the conversion of, for example, grass and corn to ensilage, etc. The polypeptides of the present invention may be used in the enzymatic hydrolysis of various plant cell wall-derived materials or waste materials, e.g., from paper production, or agricultural residues such as wheat-straw, corn cobs, corn fiber, whole corn plants, nut shells, grass, vegetable hulls, bean hulls, spent grains, sugar beet pulp, and the like. The polypeptides may also be used for modifying the viscosity of plant cell wall derived material. For instance, the polypeptides may be used to reduce the viscosity of xylan-containing material, to promote processing of viscous xylan-containing material, such as in wheat separation.

The polypeptides of the present invention may also be used with limited activity of other xylanolytic enzymes to degrade xylans for production of oligosaccharides. The oligosaccharides may be used as bulking agents, like arabinoxylan oligosaccharides released from cereal cell wall material, or of more or less purified arabinoxylans from cereals.

The polypeptides of the present invention may also be used in combination with other xylanolytic enzymes to degrade xylans to xylose and other monosaccharides (U.S. Pat. No. 5,658,765). The released xylose may be converted to other compounds.

The polypeptides of the present invention may also be used in lignocellulosic biomass degradation or conversion to fermentable sugars for the production of, for example, fuel, potable ethanol, and/or fermentation products (e.g., acids, alcohols, ketones, gases, and the like). The polypeptides are preferably used in combination with other xylan degrading enzymes and a cellulase composition (endoglucanase(s), cellobiohydrolase(s), and beta-glucosidase(s)).

The polypeptides of the present invention may be used together with other enzymes like glucanases to improve the extraction of oil from oil-rich plant material, like corn-oil from corn-embryos.

The polypeptides of the present invention may also be used in baking to improve the development, elasticity, and/or stability of dough and/or the volume, crumb structure, and/or anti-staling properties of the baked product. The polypeptides may be used for the preparation of dough or baked products prepared from any type of flour or meal (e.g., based on wheat, rye, barley, oat, or maize). The baked products produced with a polypeptide of the present invention include bread, rolls, baguettes and the like. For baking purposes a polypeptide of the present invention may be used as the only or major enzymatic activity, or may be used in combination with other enzymes such as a lipase, an amylase, an oxidase (e.g., glucose oxidase, peroxidase), a laccase and/or a protease.

The polypeptides of the present invention may also be used for modification of animal feed and may exert their effect either in vitro (by modifying components of the feed) or in vivo. The polypeptides may be added to animal feed compositions containing high amounts of arabinoxylans and glucuronoxylans, e.g., feed containing cereals such as barley, wheat, rye, oats, or maize. When added to feed the polypeptide will improve the in vivo break-down of plant cell wall material partly due to a reduction of intestinal viscosity (Bedford et al., 1993, Proceedings of the 1st Symposium on Enzymes in Animal Nutrition, pp. 73-77), whereby improved utilization of the plant nutrients by the animal is achieved. Thereby, the growth rate and/or feed conversion ratio (i.e., the weight of ingested feed relative to weight gain) of the animal is improved.

The polypeptides of the present invention may also be used in the paper and pulp industry, inter alfa in bleaching processes to enhance the brightness of bleached pulps whereby the amount of chlorine used in the bleaching stages is reduced, and to increase the freeness of pulps in the recycled paper process (Eriksson, 1990, *Wood Science and Technology* 24: 79-101; Paice et al., 1988, *Biotechnol. and Bioeng.* 32: 235-239, and Pommier et al., 1989, *Tappi Journal* 187-191). Furthermore, the polypeptides may be used for treatment of lignocellulosic pulp so as to improve the bleachability thereof. The treatment of lignocellulosic pulp may be performed, for example, as described in U.S. Pat. No. 5,658,765, WO 93/08275, WO 91/02839, and WO 92/03608.

The polypeptides of the present invention may also be used in beer brewing, in particular to improve the filterability of wort containing, for example, barley and/or sorghum malt (WO 2002/24926). The polypeptides may be used in the same manner as pentosanases conventionally used for brewing, e.g., as described by Viëtor et al., 1993, *J. Inst. Brew.* 99: 243-248; and EP 227159. Furthermore, the polypeptides may be used for treatment of brewers spent grain, i.e., residuals from beer wort production containing barley or malted barley or other cereals, so as to improve the utilization of the residuals for, e.g., animal feed.

The polypeptides of the present invention may be used for separation of components of plant cell materials, in particular of cereal components such as wheat components. Of particular interest is the separation of wheat into gluten and starch, i.e., components of considerable commercial interest. The separation process may be performed by use of methods known in the art, conveniently a so-called batter process (or wet milling process) performed as a hydroclone or a decanter process. In the batter process, the starting material is a dilute pumpable dispersion of the plant material such as wheat to be subjected to separation. In a wheat separation process the dispersion is made normally from wheat flour and water.

The polypeptides of the invention may also be used in the preparation of fruit or vegetable juice in order to increase yield.

The polypeptides of the present invention may also be used as a component of an enzymatic scouring system for textiles.

The polypeptides of the present invention may also be used in laundry detergent applications in combination with other enzyme functionalities.

Signal Peptide

The present invention also relates to nucleic acid constructs comprising a gene encoding a protein, wherein the gene is operably linked to a nucleotide sequence encoding a signal peptide comprising or consisting of amino acids 1 to 19 of SEQ ID NO: 2 or amino acids 1 to 18 of SEQ ID NO: 4, wherein the gene is foreign to the nucleotide sequence.

In a preferred aspect, the nucleotide sequence comprises or consists of nucleotides 1 to 57 of SEQ ID NO: 1. In another preferred aspect, the nucleotide sequence comprises or consists of nucleotides 1 to 54 of SEQ ID NO: 3.

The present invention also relates to recombinant expression vectors and recombinant host cells comprising such nucleic acid constructs.

The present invention also relates to methods of producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

*Thielavia terrestris* NRRL 8126 was used as the source of genes encoding Family 10 polypeptides having xylanase activity.

Media

PDA plates were composed per liter of 39 grams of potato dextrose agar.

NNCYP medium was composed per liter of 5.0 g of $NH_4NO_3$, 0.5 g of $MgSO_4.7H_2O$, 0.3 g of $CaCl_2$, 2.5 g of citric acid, 1.0 g of Bacto Peptone, 5.0 g of yeast extract, 1 ml of COVE trace metals solution, and sufficient $K_2HPO_4$ to achieve a final pH of 5.4.

NNCYPmod medium was composed per liter of 1.0 g of NaCl, 5.0 g of $NH_4NO_3$, 0.2 g of $MgSO_4.7H_2O$, 0.2 g of $CaCl_2$, 2.0 g of citric acid, 1.0 g of Bacto Peptone, 5.0 g of yeast extract, 1 ml of COVE trace metals solution, and sufficient $K_2HPO_4$ to achieve a final pH of 5.4.

COVE trace metals solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

LB plates were composed per liter of 10 g of tryptone, 5 g of yeast extract, 5 g of sodium chloride, and 15 g of Bacto Agar.

MDU2BP medium was composed per liter of 45 g of maltose, 1 g of $MgSO_4.7H_2O$, 1 g of NaCl, 2 g of $K_2HSO_4$, 12 g of $KH_2PO_4$, 2 g of urea, and 500 µl of AMG trace metals solution, the pH was adjusted to 5.0 and then filter sterilized with a 0.22 µm filtering unit.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, and 3 g of citric acid.

SOC medium was composed of 2% tryptone, 0.5% yeast extract, 10 mM NaCl, 2.5 mM KCl, 10 mM $MgCl_2$, and 10 mM $MgSO_4$, sterilized by autoclaving and then filter-sterilized glucose was added to 20 mM.

Freezing medium was composed of 60% SOC medium and 40% glycerol.

2×YT medium was composed per liter of 16 g of tryptone, 10 g of yeast extract, 5 g of NaCl, and 15 g of Bacto agar.

Example 1: Expressed Sequence Tags (EST) cDNA Library Construction

*Thielavia terrestris* NRRL 8126 was cultivated in 50 ml of NNCYPmod medium supplemented with 1% glucose in a 250 ml flask at 45° C. for 24 hours with shaking at 200 rpm. A two ml aliquot from the 24-hour liquid culture was used to seed a 500 ml flask containing 100 ml of NNCYPmod medium supplemented with 2% SIGMACELL® 20 (Sigma Chemical Co., St. Louis, Mo., USA). The culture was incubated at 45° C. for 3 days with shaking at 200 rpm. The mycelia were harvested by filtration through a funnel with a glass fiber prefilter (Nalgene, Rochester, N.Y., USA), washed twice with 10 mM Tris-HCl-1 mM EDTA pH 8 (TE), and quick frozen in liquid nitrogen.

Total RNA was isolated using the following method. Frozen mycelia of *Thielavia terrestris* NRRL 8126 were ground in an electric coffee grinder. The ground material was mixed 1:1 v/v with 20 ml of FENAZOL™ (Ambion, Inc., Austin, Tex., USA) in a 50 ml FALCON® tube. Once the mycelia were suspended, they were extracted with chloroform and three times with a mixture of phenol-chloroform-isoamyl alcohol 25:24:1 v/v/v. From the resulting aqueous phase, the RNA was precipitated by adding 1/10 volume of 3 M sodium acetate pH 5.2 and 1.25 volumes of isopropanol. The precipitated RNA was recovered by centrifugation at 12,000×g for 30 minutes at 4° C. The final pellet was washed with cold 70% ethanol, air dried, and resuspended in 500 ml of diethylpyrocarbonate treated water (DEPC-water).

The quality and quantity of the purified RNA was assessed with an AGILENT® 2100 Bioanalyzer (Agilent Technologies, Inc., Palo Alto, Calif., USA). Polyadenylated mRNA was isolated from 360 µg of total RNA with the aid of a POLY(A)PURIST™ Magnetic Kit (Ambion, Inc., Austin, Tex., USA) according to the manufacturer's instructions.

To create the cDNA library, a CLONEMINER™ Kit (Invitrogen Corp., Carlsbad, Calif., USA) was employed to construct a directional library that does not require the use of restriction enzyme cloning, thereby reducing the number of chimeric clones and size bias.

To insure the successful synthesis of the cDNA, two reactions were performed in parallel with two different concentrations of mRNA (2.2 and 4.4 µg of poly (A)$^+$ mRNA). The mRNA samples were mixed with a Biotin-attB2-Oligo(dt) primer (Invitrogen Corp., Carlsbad, Calif., USA), 1× first strand buffer (Invitrogen Corp., Carlsbad, Calif., USA), 2 µl of 0.1 M dithiothreitol (DTT), 10 mM of each dNTP, and water to a final volume of 18 and 16 µl, respectively.

The reaction mixtures were mixed and then 2 and 4 µl of SUPERSCRIPT™ reverse transcriptase (Invitrogen Corp., Carlsbad, Calif., USA) were added. The reaction mixtures were incubated at 45° C. for 60 minutes to synthesize the first complementary strand. For second strand synthesis, to each first strand reaction was added 30 µl of 5× second strand buffer (Invitrogen Corp., Carlsbad, Calif., USA), 3 µl of 10 mM of each dNTP, 10 units of *E. coli* DNA ligase (Invitrogen Corp., Carlsbad, Calif., USA), 40 units of *E. coli* DNA polymerase I (Invitrogen Corp., Carlsbad, Calif., USA), and 2 units of *E. coli* RNase H (Invitrogen Corp., Carlsbad, Calif., USA) in a total volume of 150 µl. The mixtures were then incubated at 16° C. for two hours. After the two-hour incubation 2 µl of T4 DNA polymerase (Invitrogen Corp., Carlsbad, Calif., USA) were added to each reaction and incubated at 16° C. for 5 minutes to create a bunt-ended cDNA. The cDNA reactions were extracted with a mixture of phenol-chloroform-isoamyl alcohol 25:24:1 v/v/v and precipitated in the presence of 20 µg of glycogen, 120 µl of 5 M ammonium acetate, and 660 µl of ethanol. After centrifugation at 12,000×g for 30 minutes at 4° C., the cDNA pellets were washed with cold 70% ethanol, dried under vacuum for 2-3 minutes, and resuspended in 18 µl of DEPC-water. To each resuspended cDNA sample was added 10 µl of 5× adapted buffer (Invitrogen, Carlsbad, Calif., USA), 10 µg of each attB1 adapter (Invitrogen, Carlsbad, Calif., USA), 7 µl of 0.1 M DTT, and 5 units of T4 DNA ligase (Invitrogen, Carlsbad, Calif., USA).

Ligation reactions were incubated overnight at 16° C. Excess adapters were removed by size-exclusion chromatography in 1 ml of SEPHACRYL™ S-500 HR resin (Amersham Biosciences, Piscataway, N.J., USA). Column fractions were collected according to the CLONEMINER™ Kit's instructions and fractions 3 to 14 were analyzed with an AGILENT® 2100 Bioanalyzer to determine the fraction at which the attB1 adapters started to elute. This analysis showed that the adapters began eluting around fraction 10 or 11. For the first library fractions 6-11 were pooled and for the second library fractions 4-11 were pooled.

Cloning of the cDNA was performed by homologous DNA recombination according to the GATEWAY® System protocol (Invitrogen Corp., Carlsbad, Calif., USA) using BP CLONASE™ (Invitrogen Corp., Carlsbad, Calif., USA) as the recombinase. Each BP CLONASE™ recombination reaction contained approximately 70 ng of attB-flanked-cDNA, 250 ng of pDONR™222, 2 µl of 5×BP CLONASE™ buffer, 2 µl of TE, and 3 µl of BP CLONASE™. All reagents were obtained from Invitrogen, Carlsbad, Calif., USA. Recombination reactions were incubated at 25° C. overnight.

Heat-inactivated BP recombination reactions were then divided into 6 aliquots and electroporated into ELECTROMAX™ *E. coli* DH10B electrocompetent cells (Invitrogen Corp., Carlsbad, Calif., USA) using a GENE PULSER™ (Bio-Rad Laboratories, Inc., Hercules, Calif., USA) with the following parameters: Voltage: 2.0 kV; Resistance: 200Ω; and Capacity: 25 µF. Electrophorated cells were resuspended in 1 ml of SOC medium and incubated at 37° C. for 60 minutes with constant shaking at 200 rpm. After the incubation period, the transformed cells were pooled and mixed 1:1 with freezing medium. A 200 µl aliquot was removed for library titration and then the rest of each library was aliquoted into 1.8 ml cryovials (Wheaton Science Products, Millville, N.J., USA) and stored frozen at −80° C.

Four serial dilutions of each library were prepared: $\frac{1}{100}$, $\frac{1}{1000}$, $\frac{1}{10^4}$, and $\frac{1}{10^5}$. From each dilution 100 µl were plated onto 150 mm LB plates supplemented with 50 µg of kanamycin per ml and incubated at 37° C. overnight. The number of colonies on each dilution plate was counted and used to calculate the total number of transformants in each library.

The first library contained approximately 5.4 million independent clones and the second library contained approximately 9 million independent clones.

Example 2: Template Preparation and Nucleotide Sequencing of cDNA Clones

Aliquots from both libraries described in Example 1 were mixed and plated onto 25×25 cm LB plates supplemented with 50 µg of kanamycin per ml. Individual colonies were arrayed onto 96-well plates containing 100 µl of LB supplemented with 50 µg of kanamycin per ml with the aid of a QPix Robot (Genetix Inc., Boston, Mass., USA). Forty-five 96-well plates were obtained for a total of 4320 individual clones. The plates were incubated overnight at 37° C. with shaking at 200 rpm. After incubation, 100 µl of sterile 50% glycerol was added to each well. The transformants were replicated with the aid of a 96-pin tool (Boekel, Feasterville, Pa., USA) into secondary, deep-dish 96-well microculture plates (Advanced Genetic Technologies Corporation, Gaithersburg, Md., USA) containing 1 ml of MAGNIFICENT BROTH™ (MacConnell Research, San Diego, Calif., USA) supplemented with 50 µg of kanamycin per ml in each well. The primary microtiter plates were stored frozen at −80° C. The secondary deep-dish plates were incubated at 37° C. overnight with vigorous agitation at 300 rpm on a rotary shaker. To prevent spilling and cross-contamination, and to allow sufficient aeration, each secondary culture plate was covered with a polypropylene pad (Advanced Genetic Technologies Corporation, Gaithersburg, Md., USA) and a plastic microtiter dish cover. Plasmid DNA was prepared with a Robot-Smart 384 (MWG Biotech Inc., High Point, N.C., USA) and a MONTAGE™ Plasmid Miniprep Kit (Millipore, Billerica, Mass., USA).

Sequencing reactions were performed using BIGDYE® (Applied Biosystems, Inc., Foster City, Calif., USA) terminator chemistry (Giesecke et al., 1992, *Journal of Virology Methods* 38: 47-60) and a M13 forward (−20) sequencing primer:

(SEQ ID NO: 5)
5'-GTAAAACGACGGCCAG-3'

The sequencing reactions were performed in a 384-well format with a Robot-Smart 384. Terminator removal was performed with a MULTISCREEN® Seq384 Sequencing Clean-up Kit (Millipore, Billerica, Mass., USA). Reactions contained 6 µl of plasmid DNA and 4 µl of sequencing master-mix (Applied Biosystems, Foster City, Calif., USA) containing 1 µl of 5× sequencing buffer (Millipore, Billerica, Mass., USA), 1 µl of BIGDYE® terminator (Applied Biosystems, Inc., Foster City, Calif., USA), 1.6 pmoles of M13 forward primer, and 1 µl of water. Single-pass DNA sequencing was performed with an ABI PRISM Automated DNA Sequencer Model 3700 (Applied Biosystems, Foster City, Calif., USA).

Example 3: Analysis of DNA Sequence Data of cDNA Clones

Base calling, quality value assignment, and vector trimming were performed with the assistance of PHRED/PHRAP software (University of Washington, Seattle, Wash., USA). Clustering analysis of the ESTs was performed with a Transcript Assembler v. 2.6.2. (Paracel, Inc., Pasadena, Calif., USA). Analysis of the EST clustering indicated the presence of 395 independent clusters.

Sequence homology analysis of the assembled EST sequences against the PIR and other databases was performed with the Blastx program (Altschul et. al., 1990, *J. Mol. Biol.* 215:403-410) on a 32-node Linux cluster (Paracel, Inc., Pasadena, Calif., USA) using the BLOSUM 62 matrix (Henikoff, 1992, *Proc. Natl. Acad. Sci. USA* 89: 10915-10919) From these, 246 had hits to known genes in various protein databases and 149 had no significant hits against these databases. Among these 246 genes, 13 had hits against well characterized homologues of glycosyl hydrolase genes.

Example 4: Identification of cDNA Clones Encoding *Thielavia terrestris* Family 10 Xylanases (GH10A and GH10B)

A cDNA clone encoding a *Thielavia terrestris* Family 10 xylanase (GH10A) was initially identified by sequence homology to a xylanase from *Agaricus bisporus* (GenPept accession number 060206). Another cDNA clone encoding another *Thielavia terrestris* Family 10 xylanase (GH10B) was initially identified by sequence homology to a xylanase from *Humicola grisea* (GenPept accession number BAA19220).

After this initial identification, clones designated Tter10D9 (GH10A) and Tter23D1 (GH10B) were retrieved from their original frozen stock plates and streaked onto LB plates supplemented with 50 µg of kanamycin per ml. The plates were incubated overnight at 37° C. and a single colony from each plate was used to inoculate 3 ml of LB medium supplemented with 150 µg of kanamycin per ml. The liquid cultures were incubated overnight at 37° C. and plasmid DNA was prepared from both with a BIOROBOT® 9600 (QIAGEN INC., Inc., Valencia, Calif., USA). Plasmid DNAs from clones Tter10D9 and Tter23D1 were sequenced again with BIGDYE® terminator chemistry as described above, using the M13 forward primer, the M13 reverse primer, and a Poly-T primer shown below to sequence the 3' end of the clone. 5'-TTTTTTTTTTTTTTTTTTTTTTTVN-3' (SEQ ID NO: 6), where V=G, A, C and N=G, A, C, T.

Analysis of the deduced amino acid sequence of clones 10D9 with the Interproscan program (Zdobnov and Apweiler, 2001, *Bioinformatics* 17: 847-8) showed that the amino acid sequence contained the sequence signature of the glycosyl hydrolase Family 10. This sequence signature known as the Pfam: PF00331 was found 28 amino acids from the starting amino acid methionine confirming that clone Tter10D9 encoded a Family 10 glycosyl hydrolase.

Analysis of the deduced amino acid sequence of clone 23D1 showed that this protein also contained the signature of the glycosyl hydrolase family 10 Pfam: PF00331. The signature sequence was found 18 amino acids from the starting amino methionine confirming that clone Tter23D1 encoded a Family 10 glycosyl hydrolase.

The cDNA sequence (SEQ ID NO: 1) and deduced amino acid sequence (SEQ ID NO: 2) of Tter10D9 are shown in FIG. 1. The cDNA clone encodes a polypeptide of 369 amino acids. The % G+C content of the full-length coding region is 66.3% and of the mature protein coding region (nucleotides 58 to 1107 of SEQ ID NO: 1) is 66.5%. Using the SignalP software program (Nielsen et al., 1997, *Protein Engineering* 10: 1-6), a signal peptide of 19 residues was predicted. The predicted mature protein contains 350 amino acids with a molecular mass of 39.1 kDa.

A comparative pairwise global alignment of amino acid sequences was determined using the Clustal W method (Higgins, 1989, supra) with the AlignX module of Vector NTI Advance 10.3 software (Invitrogen, Carlsbad, Calif., USA) and a blosum62mt2 scoring matrix and the following multiple alignment parameters: K-tuple size 1; best diagonals 5; window size 5; gap penalty 5; gap opening penalty 10; gap extension penalty 0.1. The alignment showed that the deduced amino acid sequence of the *Thielavia terrestris* GH10A gene shared 77% identity to the deduced amino acid sequence of a *Myceliophthora thermophila* xylanase sequence (GeneSeqP:AAW23541; WO 97/27292).

The cDNA sequence (SEQ ID NO: 3) and deduced amino acid sequence (SEQ ID NO: 4) of Tter23D1 are shown in FIG. 2. The cDNA clone encodes a polypeptide of 414 amino acids. The % G+C content of the full-length coding region is 66.7% and of the mature protein coding region (nucleotides 55 to 1242 of SEQ ID NO: 3) is 66.8%. Using the SignalP software program (Nielsen et al., 1997, supra), a signal peptide of 18 residues was predicted. The predicted mature protein contains 396 amino acids with a molecular mass of 42.5 kDa.

A comparative pairwise global alignment of amino acid sequences was determined using the Clustal W method (Higgins, 1989, supra) with the AlignX module of Vector NTI Advance 10.3 software and a blosum62mt2 scoring matrix and the following multiple alignment parameters: K-tuple size 1; best diagonals 5; window size 5; gap penalty 5; gap opening penalty 10; gap extension penalty 0.1. The alignment showed that the deduced amino acid sequence of the *Thielavia terrestris* GH10B gene shared 54% identity to the deduced amino acid sequence of the *Aspergillus aculeatus* xylanase II, (GeneSeqP:AAR63790; WO 94/21785).

Figure 4:
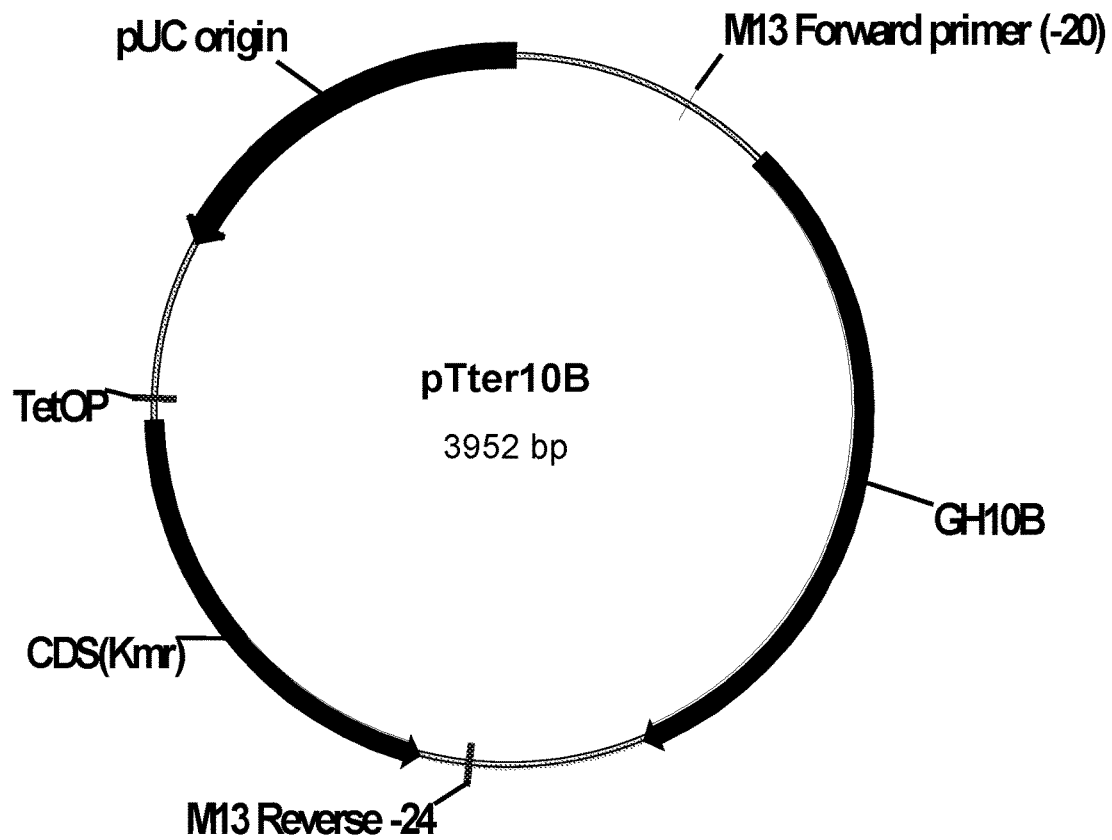
FIG. 4 shows a restriction map of pTter10B.

Once the identities of clones Tter10D9 and Tter23D1 were confirmed, a 0.5 µl aliquot of plasmid DNA from each clone designated pTter10A (FIG. 3) and pTter10B (FIG. 4) was transferred into separate vials of *E. coli* TOP10 cells (Invitrogen Corp., Carlsbad, Calif., USA), gently mixed, and incubated on ice for 10 minutes. The cells were then heat-shocked at 42° C. for 30 seconds and incubated again on ice for 2 minutes. The cells were resuspended in 250 µl of SOC medium and incubated at 37° C. for 60 minutes with constant shaking at 200 rpm. After the incubation period, two 30 µl aliquots were plated onto LB plates supplemented with 50 µg of kanamycin per ml and incubated overnight at 37° C. The next day a single colony was picked from each transformation and streaked onto three 1.8 ml cryovials containing about 1.5 mls of LB agarose supplemented with 50 µg of kanamycin per ml. The vials were sealed with PETRISEAL™ (Diversified Biotech, Boston Mass., USA) and deposited with the Agricultural Research Service Patent Culture Collection, Northern Regional Research Center, Peoria, Ill., USA, as NRRL B-50079 and NRRL B-50080 with a deposit date of Nov. 30, 2007.

Deposits of Biological Material

The following biological materials have been deposited under the terms of the Budapest Treaty with the Agricultural Research Service Patent Culture Collection (NRRL), Northern Regional Research Center, 1815 University Street, Peoria, Ill., 61604, USA, and given the following accession numbers:

| Deposit | Accession Number | Date of Deposit |
| --- | --- | --- |
| E. coli pTter10A | NRRL B-50079 | Nov. 30, 2007 |
| E. coli pTter10B | NRRL B-50080 | Nov. 30, 2007 |

The strains have been deposited under conditions that assure that access to the culture will be available during the pendency of this patent application to one determined by foreign patent laws to be entitled thereto. The deposits represent a substantially pure culture of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method for degrading a xylan-containing material, comprising treating the xylan-containing material with a polypeptide having xylanase activity, wherein the polypeptide having xylanase activity is selected from the group consisting of:
   (a) a polypeptide having at least 90% sequence identity to the sequence of amino acids 20 to 369 of SEQ ID NO: 2 or amino acids 19 to 414 of SEQ ID NO: 4;
   (b) a polypeptide encoded by a polynucleotide that hybridizes under high stringency conditions with the full-length complement of the sequence of nucleotides 58 to 1107 of SEQ ID NO: 1 or nucleotides 55 to 1242 of SEQ ID NO: 3, wherein high stringency conditions are defined as prehybridization and hybridization at 42° C. in 5×SSPE, 0.3% SDS, 200 µg/ml sheared and denatured salmon sperm DNA, and 50% formamide, followed by three washing steps each for 15 minutes using 2×SSC, 0.2% SDS at 65° C.; and
   (c) a polypeptide encoded by a polynucleotide having at least 90% sequence identity to the sequence of nucleotides 58 to 1107 of SEQ ID NO: 1 or nucleotides 55 to 1242 of SEQ ID NO: 3.

2. The method of claim 1, wherein the polypeptide has at least 95% sequence identity to the sequence of amino acids 20 to 369 of SEQ ID NO: 2 or amino acids 19 to 414 of SEQ ID NO: 4.

3. The method of claim 1, wherein the polypeptide has at least 96% sequence identity to the sequence of amino acids 20 to 369 of SEQ ID NO: 2 or amino acids 19 to 414 of SEQ ID NO: 4.

4. The method of claim 1, wherein the polypeptide has at least 97% sequence identity to the sequence of amino acids 20 to 369 of SEQ ID NO: 2 or amino acids 19 to 414 of SEQ ID NO: 4.

5. The method of claim 1, wherein the polypeptide has at least 98% sequence identity to the sequence of amino acids 20 to 369 of SEQ ID NO: 2 or amino acids 19 to 414 of SEQ ID NO: 4.

6. The method of claim 1, wherein the polypeptide has at least 99% sequence identity to the sequence of amino acids 20 to 369 of SEQ ID NO: 2 or amino acids 19 to 414 of SEQ ID NO: 4.

7. The method of claim 1, wherein the polypeptide is a fragment of the amino acid sequence of SEQ ID NO: 2, SEQ ID NO: 4, amino acids 20 to 369 of SEQ ID NO: 2, or amino acids 19 to 414 of SEQ ID NO: 4 having xylanase activity.

8. The method of claim 1, wherein the polypeptide comprises the sequence of SEQ ID NO: 2 or SEQ ID NO: 4.

9. The method of claim 1, wherein the polypeptide comprises the sequence of amino acids 20 to 369 of SEQ ID NO: 2 or amino acids 19 to 414 of SEQ ID NO: 4.

10. The method of claim 1, wherein the polypeptide is encoded by a polynucleotide that hybridizes under very high stringency conditions with the full-length complement of the sequence of nucleotides 58 to 1107 of SEQ ID NO: 1 or nucleotides 55 to 1242 of SEQ ID NO: 3, wherein very high stringency conditions are defined as prehybridization and hybridization at 42° C. in 5×SSPE, 0.3% SDS, 200 µg/ml sheared and denatured salmon sperm DNA, and 50% formamide, followed by three washing steps each for 15 minutes using 2×SSC, 0.2% SDS at 70° C.

11. The method of claim 1, wherein the polypeptide is encoded by a polynucleotide comprising the sequence of nucleotides 58 to 1107 of SEQ ID NO: 1 or nucleotides 55 to 1242 of SEQ ID NO: 3.

12. The method of claim 1, further comprising treating the material comprising the xylan-containing material with a xylan degrading enzyme.

13. The method of claim 12, wherein the xylan degrading enzyme is one or more enzymes selected from the group consisting of an acetylxylan esterase, an arabinofuranosidase, a xylosidase, a feruloyl esterase, and a glucuronidase.

14. The method of claim 1, wherein the xylan-containing material is an animal feed.

15. The method of claim 1, wherein the xylan-containing material is a Kraft pulp.

16. The method of claim 1, wherein the xylan-containing material is a cellulosic or lignocellulosic biomass.

* * * * *